United States Patent [19]

Gsell et al.

[11] Patent Number: 5,695,653
[45] Date of Patent: Dec. 9, 1997

[54] DEVICE AND METHOD FOR SEPARATING COMPONENTS FROM A BIOLOGICAL FLUID

[75] Inventors: Thomas C. Gsell, Glen Cove; Thomas J. Bormann, Melville; Vlado I. Matkovich, Glen Cove, all of N.Y.

[73] Assignee: Pall Corporation, East Hills, N.Y.

[21] Appl. No.: 362,406

[22] Filed: Dec. 23, 1994

[51] Int. Cl.⁶ .................. B01D 37/00; B01D 36/00
[52] U.S. Cl. .............. 210/767; 210/195.1; 210/252; 210/258; 210/435; 210/650; 210/805
[58] Field of Search ....................... 210/650, 767, 210/805, 195.1, 195.2, 252, 258, 435, 651

[56] References Cited

U.S. PATENT DOCUMENTS

| | | | |
|---|---|---|---|
| 3,098,819 | 7/1963 | Sager | 210/97 |
| 3,705,100 | 12/1972 | Blatt et al. | |
| 3,892,236 | 7/1975 | Djerassi. | |
| 4,178,248 | 12/1979 | Porter et al. | 210/167 |
| 4,196,070 | 4/1980 | Chao et al. | 204/266 |
| 4,411,792 | 10/1983 | Babb | 210/651 |
| 4,466,705 | 8/1984 | Michelson | 350/418 |
| 4,655,742 | 4/1987 | Vantard | 604/6 |
| 4,687,580 | 8/1987 | Malbrancq et al. | 210/651 |
| 4,751,007 | 6/1988 | Kobayashi et al. | 210/791 |
| 4,753,733 | 6/1988 | Ramstack | 210/636 |
| 4,769,150 | 9/1988 | Ramstack | 210/636 |
| 4,800,022 | 1/1989 | Leonard | 210/636 |
| 4,936,998 | 6/1990 | Nishimura et al. | 210/638 |
| 5,141,490 | 8/1992 | Fujii et al. | 604/6 |
| 5,143,630 | 9/1992 | Rolchigo | 210/780 |
| 5,217,627 | 6/1993 | Pall et al. | 210/767 |
| 5,223,439 | 6/1993 | Rolle | 436/177 |
| 5,476,587 | 12/1995 | Kuroki et al. | 210/496 |

FOREIGN PATENT DOCUMENTS

| | | |
|---|---|---|
| 0132210 | 1/1985 | European Pat. Off. |
| 8605410 | 9/1986 | WIPO. |
| 88/02641 | 4/1988 | WIPO. |
| 89/03696 | 5/1989 | WIPO. |
| 9308904 | 5/1993 | WIPO. |
| 9401193 | 1/1994 | WIPO. |

*Primary Examiner*—John Kim
*Attorney, Agent, or Firm*—Leydig, Voit & Mayer, Ltd.

[57] ABSTRACT

A system for processing a biological fluid by spirally passing the biological fluid along at least one first flow path along the first surface of a separation medium in a separation device is disclosed. Also disclosed is a system for processing a biological fluid utilizing a plurality of pressure differential generators including enclosed chambers.

14 Claims, 4 Drawing Sheets

DEVICE AND METHOD FOR SEPARATING COMPONENTS FROM A BIOLOGICAL FLUID

TECHNICAL FIELD

The present invention relates to processing a biological fluid such as blood. Preferably, the present invention provides for separating at least one component from the biological fluid.

BACKGROUND OF THE INVENTION

An adult human contains about 5 liters of blood, of which red blood cells account for about 45% of the volume, white cells about 1%, and the balance being liquid blood plasma. Blood also contains large numbers of platelets. In view of the substantial therapeutic and monetary value of blood components such as red blood cells, platelets, and plasma, a variety of techniques have been developed to separate blood into its component fractions while ensuring maximum purity and recovery of each of the components.

Many techniques for the separation of a biological fluid into one or more components include the use of centrifugation at least once during the separation process. For example, donated blood may be collected into a blood collection bag and separated by centrifugation to produce PRC (packed red cell) and PRP (platelet-rich plasma) fractions. PRP may be centrifuged to concentrate the platelets, so that PC (platelet concentrate) may be prepared. In other techniques, for example, during apheresis protocols, blood may be centrifuged and/or exposed to a rotating device to separate and harvest at least one desired component, and the remainder of the blood is returned to the donor.

These techniques suffer from a number of drawbacks. For example, the forces of centrifugation may stress blood components such as platelets and/or red blood cells. Additionally, some systems require the use of peristaltic pumps to transfer the biological fluid from one location to another. The operation of the peristaltic pump involves repeated compression of at least one fluid filled flexible tube, which may cause damage, e.g., hemolysis, to blood components such as red blood cells, as the tube is compressed.

Moreover, even those techniques that provide for non-centrifugal separation suffer from a number of deficiencies. For example, some systems require the use of devices that stress or damage the components. Additionally, some devices are inefficient and/or bulky. Illustratively, some non-centrifugal techniques for separating a biological fluid into one or more components produce reduced yields and/or subject the components to undesirable stresses by utilizing separation devices that provide for less efficient fluid flow toward the porous membrane within the separation device. For example, some separation devices utilize fluid flow channels having sections that include flat or straight walls and/or sharp edges to direct the fluid toward the membrane, and components such as platelets and/or red blood cells may be stressed or damaged upon contacting these walls or edges. These flow channels may provide for less efficient fluid flow and/or separation by reducing fluid velocity, creating stagnant areas of fluid, and/or exposing less of the surface of the membrane to the fluid. As a result, these systems may not only stress or damage blood components, but they may suffer from reduced yields due to membrane fouling.

Accordingly, there is an unmet need for a system and process that provides for efficient separation while decreasing the potential for damaging blood components by avoiding the stresses caused by centrifugation and/or peristaltic pumping. It would also be desirable to produce separated, leukocyte-depleted and therapeutically effective blood components in high yield, without centrifugation, and, more preferably, without peristaltic pumping.

The present invention ameliorates at least some of the disadvantages of the prior art component separation protocols. These improvements in processing biological fluid, and other advantages of the present invention, will be apparent from the description as set forth below.

SUMMARY OF THE INVENTION

In accordance with the invention, a plurality of pressure differential generators including enclosed chambers create pressure differentials sufficient to cause a biological fluid including plasma and at least one other component of the biological fluid to flow back and forth to a separation device including a separation medium, for separation of the biological fluid into a plasma-rich fraction and a plasma-depleted fraction, without subjecting the fluid to the stresses caused by rotation, spinning, centrifugation or peristaltic pumping. Accordingly, the present invention directly and effectively minimizes or eliminates loss or damage to biological fluid components such as platelets and/or red blood cells caused by the currently used separation processes. In a preferred embodiment, the instant invention also provides for leukocyte depletion of at least one component of the biological fluid.

In some embodiments, preferably including the use of at least one pressure differential generator including an enclosed chamber to pass a biological fluid including plasma and at least one other component of the biological fluid to a separation device including a separation medium, the biological fluid is spirally passed along a first surface of a separation medium having a first surface and a second surface, so that plasma and at least one other component pass along the first surface of the medium, and a portion of plasma passes from the first surface of the separation medium to the second surface of the separation medium. Accordingly, the biological fluid is separated into a plasma-rich fraction and a plasma-depleted fraction, while minimizing the stresses to the biological fluid components by avoiding contact with flat or straight walls or sharp edges within the separation device. This embodiment may also provide for increased separation efficiency.

In a more preferred embodiment, a plurality of pressure differential generators including enclosed chambers create pressure differentials sufficient to cause the biological fluid to flow back and forth to a separation device, and to spirally pass the biological fluid to the first surface of the separation medium in the separation device.

Advantages provided by embodiments of the invention provide for reduced stress and/or damage to the components of the biological fluid, e.g., red cells and/or platelets, while providing efficient separation of plasma from these other components. In some embodiments, platelet activation may be minimized. Accordingly, the present invention may provide for increased yield of clinically and therapeutically superior red cells, platelet concentrate and/or cell-free plasma.

In accordance with the methods, systems, and devices provided by the invention, plasma is efficiently separated from at least one other component of the biological fluid, with minimal loss of separation medium efficiency. The present invention may provide for minimizing or reducing the fouling of the separation medium.

In describing the present invention, the following terms are used as defined below.

(A) Biological Fluid: A biological fluid includes any treated or untreated fluid associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); analogous blood products derived from blood or a blood component or derived from bone marrow; red cells separated from plasma and resuspended in physiological fluid; and platelets separated from plasma and resuspended in physiological fluid. The biological fluid may include leukocytes, or may be treated to remove, isolate, or obtain leukocytes or other components of the biological fluid. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation. Typically, the volume of a unit varies, the amount differing from patient to patient and from donation to donation. Multiple units of some blood components, particularly platelets and buffy coat, may be pooled or combined, typically by combining four or more units.

B) Plasma-Depleted Fluid: A plasma-depleted fluid refers to a biological fluid which has had some quantity of plasma-rich fluid (defined below) removed therefrom, e.g., the platelet-rich fluid or platelet component obtained when plasma is separated from PRP, or the fluid obtained after plasma is separated from whole blood. In some embodiments, for example, involving the processing of red cell-containing platelet-depleted fluid, the plasma-depleted fluid is the red cell-containing fluid which remains after plasma is removed from red cell-containing platelet-depleted blood. The separation of the plasma-rich fluid from the biological fluid produces a plasma-depleted fluid having an increased concentration of platelets and/or red cells on a volume basis.

C) Plasma-Rich Fluid: A plasma-rich fluid refers to the plasma portion or plasma component removed from a biological fluid, e.g., the plasma-rich fluid when plasma is separated from PRP, the plasma which is separated from whole blood, or the plasma which is separated from red cell-containing platelet-depleted fluid. The plasma-rich fluid separated from a biological fluid is typically cell-free and has an increased concentration of plasma on a volume basis. Typically, the plasma-rich fluid is the plasma-containing fluid that passes through a separation medium. Exemplary plasma-rich fluids include platelet-poor plasma or platelet-free plasma.

D) Separation medium: A separation medium refers to a porous medium having a first surface and a second surface through which at least a plasma portion or component passes, and which separates one component of the biological fluid from another component as the biological fluid is passed along the first surface of the separation medium.

As noted in more detail below, the separation medium for use with a biological fluid may be formed from any natural or synthetic fiber or from a porous or permeable membrane (or from other materials of similar surface area and pore structure or arrangement, e.g., pore size or pore rating or pore diameter) compatible with a biological fluid, typically a biological fluid containing plasma as well as platelets and/or red blood cells, e.g., whole blood or PRP. The surface of the fibers or membrane may be unmodified or may be modified to achieve a desired property.

Although the separation medium may remain untreated and/or unmodified, in some embodiments the fibers or membrane may be treated to make them even more effective for separating one component of a biological fluid, e.g., plasma, from other components of a biological fluid, e.g., platelets and/or red cells. For example, the separation medium may be treated in order to reduce or eliminate platelet adherence to the medium. Furthermore, the medium may be surface modified in order to achieve a desired critical wetting surface tension (CWST) and to be less adherent of platelets, e.g., as disclosed in U.S. Pat. Nos. 4,880,548 and 5,100,564, and International Publication No. WO 92/07656. The medium may be subjected to gas plasma treatment, as disclosed in, for example, U.S. Pat. No. 5,258,127, and International Publication No. WO 93/04673, an exemplary purpose for which is to modify the CWST, and/or to reduce platelet and/or red cell adhesion.

Defined in terms of CWST, a preferred range of CWST for a separation medium as provided by the present invention is above about 53 dynes/cm, typically above about 60 dynes/cm. The CWST of the separation medium may be dictated by its intended use.

The separation medium may be pre-formed, single or multi-layered, and/or may be treated to modify the surface of the medium. The separation medium may include at least one support and/or drainage layer. If a fibrous medium is used, the fibers may be treated either before or after forming the fibrous lay-up. It is preferred to modify the fiber surfaces before forming the fibrous lay-up because a more cohesive, stronger product is obtained after hot compression to form an integral element.

The separation medium may be configured in any suitable fashion, such as at least one of a flat sheet, a composite of two or more layers, a corrugated sheet, a web, and hollow fibers. A preferred separation medium is configured as a membrane, more preferably, a planar membrane.

SPECIFIC DESCRIPTION OF THE INVENTION

The present invention provides a method for treating a biological fluid comprising placing a container of biological fluid in an enclosed chamber of a pressure differential generator, wherein the container is in fluid communication with a separation device, said device including a separation medium having a first surface and a second surface, and at least one spiral first flow path along the first surface of the separation medium; varying the pressure within the chamber which is exerted on the container to vary the volume of the container and force fluid out of the container to the separation device; passing the biological fluid along the first spiral flow path in the separation device along the first surface of the separation medium; passing a plasma-rich fluid from the first surface of the separation medium through the separation medium to a second surface of the separation medium, and passing a plasma-depleted fluid along the first surface of the separation medium and out of the device.

Preferably, the method includes passing the biological fluid along two or more spiral flow paths along the first surface of the separation medium. In a more preferred embodiment, the method includes spirally passing the fluid along two or more fluid flow channels along the first surface of the separation medium.

In one embodiment, the plasma-depleted fluid is passed from the separation device into an additional container for holding plasma-depleted fluid. In a more preferred embodiment, this additional container is in an enclosed chamber of an additional pressure differential generator, and the method further comprises varying the pressure within the chamber which is exerted on the container to vary the volume of the container and force fluid out of the additional container to the separation device.

In an embodiment of a method according to the invention, two or more pressure differential generators each comprising an enclosed chamber suitable for containing a variable volume container capable of holding a biological fluid, provide for passing the biological fluid from a container to a separation device including a separation medium, passing the biological fluid along at least one first flow path in the separation device along a first surface of the separation medium; passing a plasma-rich fluid from the first surface of the separation medium through the separation medium to a second surface of the separation medium, and passing a plasma-depleted fluid along the first surface of the separation medium and out of the device. Preferably, passing the biological fluid along the first fluid flow path includes spirally passing the fluid along at least one fluid flow channel along the first surface of the separation medium.

Embodiments of the method may also include depleting leukocytes from the biological fluid, for example, by passing the biological fluid through a leukocyte depletion medium, before or after passing the fluid to the separation device. The method may include depleting leukocytes from the plasma-rich fluid and/or the plasma-depleted fluid. In one preferred embodiment, a biological fluid is leukocyte-depleted, and separated into a plasma-rich fluid and a plasma-depleted fluid, without exposing the biological fluid to either the stress of centrifugation or the stress of peristaltic pumping.

A method in accordance with the invention includes creating a first pressure differential and passing a biological fluid including plasma and at least one other component of the biological fluid from a first container to a separation device comprising a housing and a separation medium having a first surface and a second surface; passing the biological fluid along at least one first fluid flow path in the separation device along the first surface of the separation medium; passing a plasma-rich fluid along at least one second fluid flow path from the first surface of the separation medium through the separation medium to a second surface of the separation medium, and passing a plasma-depleted fluid along the first fluid flow path along the first surface of the separation medium through the separation device, and into a second container; and creating a second pressure differential and passing the plasma depleted fluid from the second container to the separation device.

The present invention provides a separation device comprising a housing including a biological fluid inlet, a plasma-depleted fluid outlet, and a plasma-rich fluid outlet, said device including a separation medium having a first surface and a second surface, and at least one spiral first flow path from the biological fluid inlet to the first surface of the separation medium and to the plasma-depleted fluid outlet, and at least one second flow path from the inlet through the separation medium to the plasma-rich fluid outlet. In a more preferred embodiment, the device includes two or more spiral first flow paths from the biological fluid inlet to the first surface of the separation medium.

The present invention provides a system for separating a quantity of at least one component, e.g., plasma, red blood cells, and/or platelets, from a biological fluid, said system comprising a separation device including a separation medium having a first surface and a second surface; and two or more pressure differential generators comprising enclosed chambers suitable for enclosing a container, such as a blood collection bag and/or a satellite bag. Preferably, the system includes at least two containers in fluid communication with the separation device. In a more preferred embodiment, the system includes three containers in fluid communication with the separation device, and at least two of the containers are variable volume containers suitable for placement within the enclosed chambers of the pressure differential generators.

In another embodiment, the present invention provides a system comprising a separation device including a separation medium having a first surface and a second surface, and providing at least one spiral first flow path along the first surface; and at least one pressure differential generator comprising an enclosed chamber suitable for enclosing a container capable of holding a biological fluid, such as a blood collection bag and/or a satellite bag.

In yet another embodiment, a system according to the invention comprises a separation device including at least one spiral first flow path, and, in fluid communication therewith, a leukocyte depletion filter assembly including a leukocyte depletion medium.

Exemplary biological fluid processing systems, which are preferably sterile, more preferably closed and sterile, are shown in FIGS. 1, 2, and 8–10.

Figure 1:
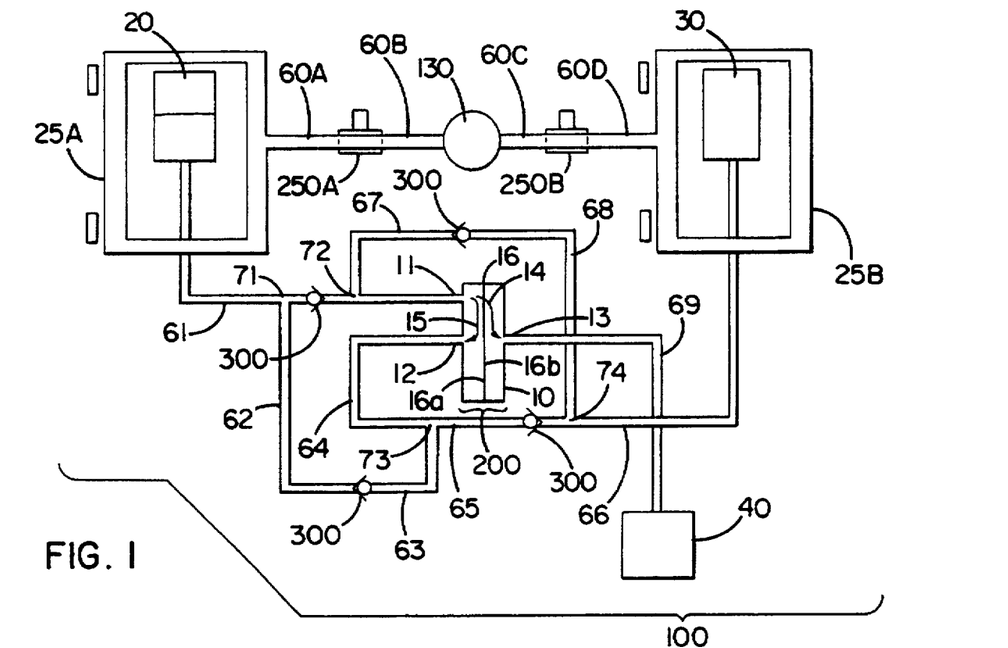
FIG. 1 is a schematic representation of an embodiment of a system according to the present invention allowing the passage of biological fluid from a first container associated with a first pressure differential generator to a second container associated with a second pressure differential generator.

Biological fluid processing system 100 typically includes a first container such as a collection bag 20; a separation device 200 including a separation medium 16, having a first surface 16a and a second surface 16b; a second container (first satellite bag) 30; and a third container (second satellite bag) 40. Fluid communication between the components or elements of the biological fluid processing system is provided through at least one conduit and/or at least one connector connecting the components. For example, as illustrated in FIG. 1, conduits 60A–60D, and 61–69, as well as connectors 71–74, provide fluid communication between the components of the system.

The system also includes at least one pressure differential generator 25A and/or 25B (FIGS. 1, 10, and 11), and/or 500 (FIGS. 8 and 9) for creating a pressure differential sufficient to force or draw fluid through the separation device 200. In some embodiments, at least one pressure differential creates a pressure differential sufficient to force or draw fluid through a leukocyte depletion filter assembly.

In a preferred embodiment, pressure differential generator 25A and/or 25B comprises an expressor including an enclosed chamber suitable for enclosing a variable volume container, such as a flexible blood collection or satellite bag, e.g., container 20 and/or 30. In a more preferred embodiment, the system may also include at least one pressure regulating mechanism 130 communicating with at least one pressure differential generator 25A, 25B to provide for controlling and/or monitoring the pressure differential.

Figure 8:
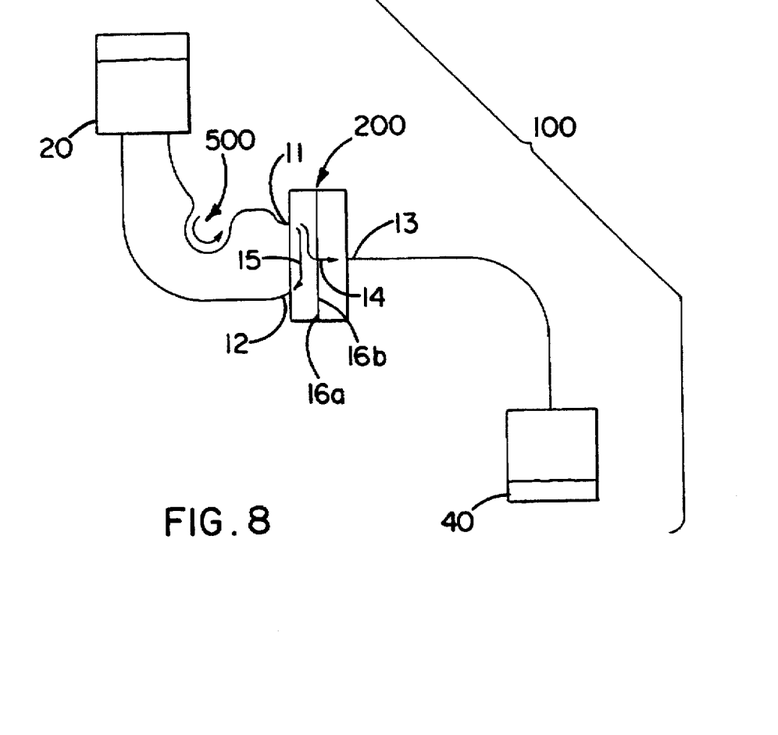
FIG. 8 is a schematic representation of another embodiment of a system according to the present invention.
Figure 9:
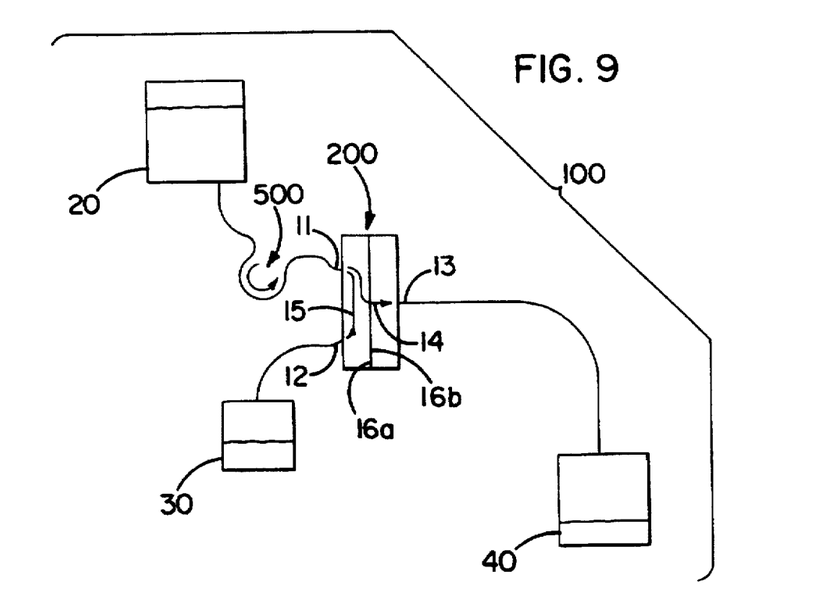
FIG. 9 is a schematic representation of another embodiment of a system according to the present invention.

In some embodiments, for example, as illustrated in FIGS. 8 and 9, at least one pressure differential generator 500 may be a pump, such as a peristaltic pump. Alternatively, at least one pressure differential generator may be a conventional expressor (e.g., lacking an enclosed chamber).

The biological fluid processing system may also include at least one flow control device such as a seal, valve, check valve, clamp, transfer leg closure, stopcock, or the like located within or on at least one of the conduits, the containers, and/or between a pressure regulating mechanism and a chamber of a pressure differential generator.

In one preferred embodiment of a system in accordance with the invention, as illustrated in FIG. 1, biological fluid processing system 100 includes at least one, and more preferably two, flow control devices 250A, 250B, such as three-way valves. Additionally, a system may include at least one, and more preferably, two or more, flow control devices 300 such as one-way check valves. The system illustrated in FIG. 1 includes four flow control devices 300, allowing flow in the direction of the arrow.

As illustrated in FIGS. 1, and 3–7, a preferred separation device 200 as provided by the invention generally comprises a housing 10 which includes a biological fluid inlet 11, a first outlet 12 (plasma-depleted fluid outlet), and a second outlet 13 (plasma-rich fluid outlet); a first fluid flow path 15 between the inlet 11 and the first outlet 12; and a second fluid flow path 14 between the inlet 11 and the second outlet 13. A separation medium 16 having first and Second surfaces 16a, 16b is positioned inside the housing 10, the separation medium being positioned parallel to the first fluid flow path 15 and across the second fluid flow path 14.

The system may also include at least one leukocyte depletion filter assembly including a leukocyte depletion medium, more preferably a fibrous porous leukocyte depletion medium. For example, the system may include at least one leukocyte depletion filter assembly upstream and/or downstream of the separation device 200, e.g., near inlet 11 and/or outlet 12; as well as between outlet 13 and container 40. Accordingly, biological fluid may be collected in first container 20, and at least a portion of the biological fluid can be leukocyte depleted and passed through the separation device 200.

Figure 2:
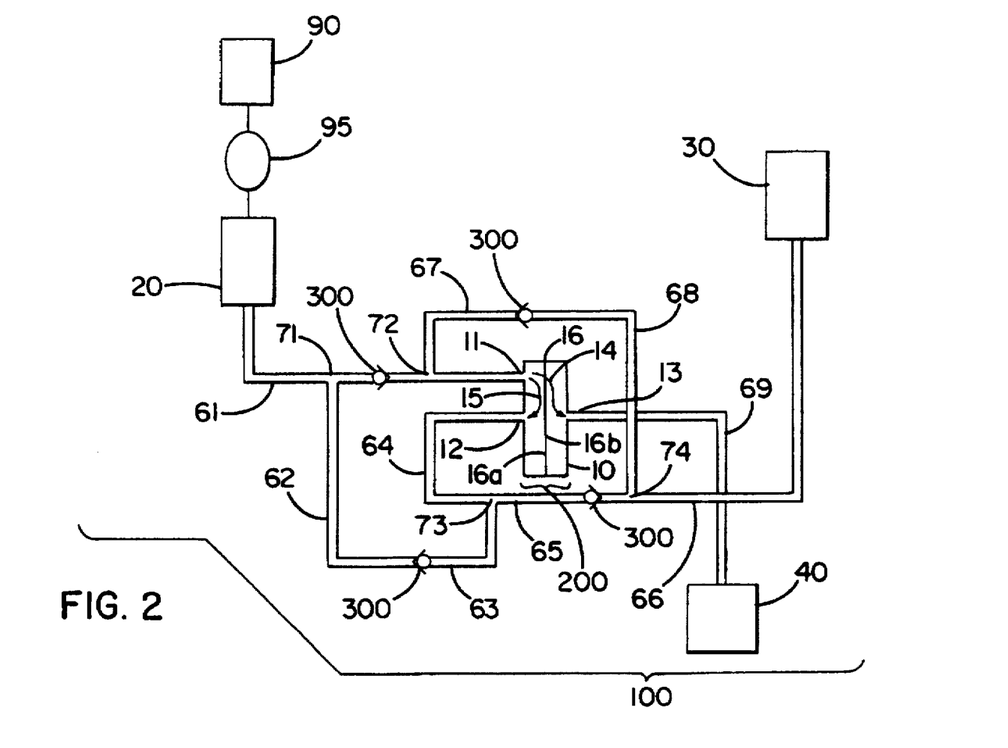
FIG. 2 is a schematic representation of an embodiment of a system according to the present invention allowing the passage of a biological fluid from one container through a leukocyte depletion filter assembly to an additional container, wherein the additional container is associated with a first pressure differential generator.

Alternatively, or additionally, the system may include a leukocyte depletion filter assembly 95 to allow leukocyte depletion of the biological fluid before collecting the fluid in a container such as first container 20. Illustratively, as illustrated in FIG. 2, the system 100 may include containers 90 and 20, with the leukocyte depletion filter assembly 95 interposed between the containers, so that the biological fluid can be leukocyte depleted and collected in container 20. The leukocyte depleted biological fluid may be passed from first container 20 to other components of the system, e.g., through conduit 61 and separation device 200.

Each of the components of the invention will now be described in more detail below.

In accordance with the invention, any container for holding processed and/or unprocessed biological fluid may be used. Preferably, the containers 20, 30, 40, and 90 are variable volume containers, e.g., flexible containers. Suitable containers include, but are not limited to conventional blood collection and satellite bags. Similarly, any conduit; connector; check valve and the like suitable for passing a biological fluid therethrough may be used according to the invention. Preferred conduits 61–69 include flexible tubing conventionally utilized for passing blood or blood components therethrough. A variety of suitable connectors 71–74, and flow control devices 300 such as one-way check valves, are known in the art.

Similarly, a variety of conduits 60A–60D, and flow control devices 250A and 250B such as three-way valves, are also known in the art. Preferably, conduits 60A–60D and flow control devices 250A and 250B are suitable for use in pneumatic systems.

PRESSURE DIFFERENTIAL GENERATOR

In accordance with the invention, the pressure differential generator provides for a pressure differential between the source of the fluid, and the intended destination of the fluid. For example, the pressure differential generator provides for a pressure differential between the first container 20 and the second container 30 of the biological fluid separation system 100, so as to draw or force biological fluid through the separation device 200. While a pressure differential may be generated by, for example, a gravity head, in a preferred embodiment, the pressure differential generator comprises a device, apparatus, or assembly that creates a pressure differential.

Figure 11:
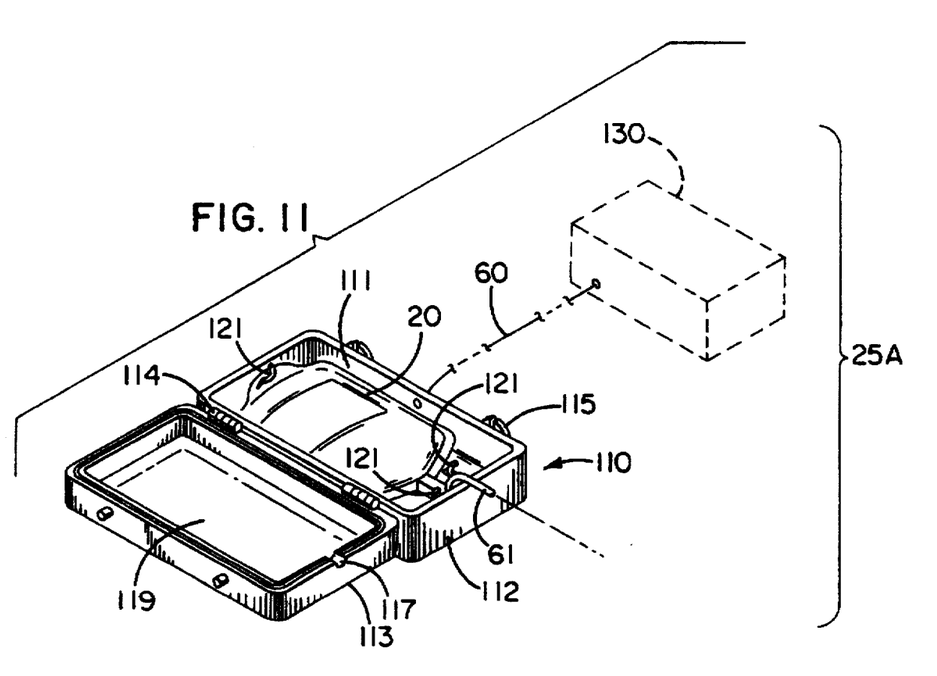
FIG. 11 is a schematic representation of a pressure differential generator including an enclosed chamber according to the present invention.

In an even more preferred embodiment, as illustrated in FIG. 11, the pressure differential generator 25A comprises an expressor including an enclosed chamber for containing a variable volume container suitable for holding a biological fluid. Such an expressor is preferred as it applies even pressure to the container, and thus avoids or minimizes creating wrinkles and folds in the bag caused by conventional expressors, which apply an uneven pressure. Since biological fluid can become trapped in these wrinkles and folds, conventional expressors prevent 100% of the fluid from being expressed.

The preferred expressor may provide other advantages over conventional expressors, since it may allow fluid to be drawn into a container, and/or minimize disturbing the interface between components of the biological fluid, e.g., between a supernatant layer and a sediment layer.

Accordingly, a preferred expressor comprises a housing defining an enclosed chamber for accommodating a variable-volume container, the housing having at least one opening through which at least one conduit (e.g., a conduit connected to the variable-volume container) can extend. Preferably, the expressor includes a pressure regulating mechanism communicating with the housing to vary the pressure of fluid in the chamber and thereby vary the volume of the container.

As shown in FIG. 11, an exemplary expressor for use in the present invention comprises a housing 110 which defines an enclosed chamber 111 and a pressure regulating mechanism 130 pneumatically coupled to the housing 110 by at least one flexible hose 60 or other conduit to vary the pressure within the chamber 111. In some embodiments, e.g., as shown in FIG. 1, which includes two expressors, each having an enclosed chamber, flexible hoses 60A, 60B, 60C and 60D provide fluid communication between the pressure regulating mechanism and the enclosed chambers of the expressors. In other embodiments (not shown) both expressors may be arranged within a single unit, e.g., including subunits with a chamber enclosed within each subunit.

A variable volume fluid container, such as a collection or satellite bag 20 containing a biological fluid (containers 30 and 90 may be utilized in a similar manner), may be placed in the chamber 111 with one or more sections of flexible tubing 61 extending from the collection bag 20 through an opening 117 in the housing 110 to the exterior of the housing 110. The collection or satellite bag 20 need not be flexible, but it preferably is constructed so that its internal volume can be varied by controlling the fluid pressure applied to the outside surface of the bag 20. The pressure regulating mechanism 130 supplies and/or withdraws a fluid (i.e., either a gas or a liquid) to and/or from the chamber 111 in order to vary the pressure exerted on the collection bag 20 within the chamber 111. This, in turn, varies the volume of the bag 20 and thereby forces fluid (i.e., either a liquid or a gas) out of or into the collection or satellite bag 20 through the flexible tubing 61. In some embodiments (not shown) the bag within the chamber may include at least one additional flexible tube, so that fluid may enter or exit the bag through tubing 61 and/or the additional tubing.

The pressure regulating mechanism 130 may include a valve arrangement such as at least one flow control device, e.g., at least one pneumatic valve, capable of connecting flexible hose 60 to the pressure source. Illustrative pneumatic valves include three way and four way pneumatic valves. In one embodiment, including the use of a standard piston pump, the valve arrangement includes at least one four way pneumatic valve capable of connecting flexible hose 60 to the input or to the output of the pump. The three-way and/or four-way pneumatic valves may electronically controlled by a control unit (not shown). Additionally, there may be a plurality of relief valves and a pressure sensor electronically controlled and monitored by the control unit. In this manner, the control unit may control and monitor the pressure or vacuum exerted on the collection or satellite bag 20. The pneumatic valve(s), the plurality of relief valves, and the pressure sensor may be, for example, disposed in the control unit, the pressure regulating mechanism 130, and/or the housing 110.

The housing 110 may be formed from any suitable material which has sufficient structural integrity to withstand the differences in pressure between the chamber 111 and the exterior of the housing 110. The housing 110 may have a variety of configurations. For example, in the expressor shown in FIG. 11, the housing 110 comprises a base 112 and a cover 113 which may be releasably mounted to the base 112 in any suitable manner to form the chamber 111 and envelop the bag 20. In the exemplary expressor, the cover 113 is releasably mounted to the base 112 by means of hinges 114 on one side of the base 112 and cover 113 and at least one and preferably two latches 115 on the other side.

The housing also preferably includes a transparent portion positioned to permit observation of the fluid container. For example, the transparent portion may be a window 119 in the cover 113. Alternatively, the entire housing by be formed from a transparent material such as a transparent plastic.

The collection or satellite bag 20 may be retained or arranged within the chamber in any suitable manner. For example, one or more securing or clamping mechanisms such as pins, clips, straps and/or hooks may be utilized to hold or restrain the bag in the chamber. Typically, one or more pins, clips, straps and or hooks may be mounted inside the chamber at the same end as the flexible tubing 61 and/or at the end opposite from the flexible tubing 61. A preferred embodiment includes at least one of a pin, clip, strap and hook at the end opposite the flexible tubing 61.

In some embodiments, a plurality of pins, clips, straps and/or hooks better secures the collection bag 20 within the housing and facilitates expression of fluid from the collection bag 20.

The embodiment illustrated in FIG. 11 includes a plurality of hooks 121 inside the chamber 111. A single hook 121 is provided on the end of the collection bag 20 opposite to the flexible tubing 61, and two hooks 121 are utilized on the end of the collection bag nearest the flexible tubing 61. The use of a plurality of clamping or securing mechanisms may be preferred if embodiments of the invention include inverting the housing 110 so that the end opposite the flexible tubing 61 is facing up, e.g., to move or mix fluid within the collection bag 20. In these embodiments, the collection bag 20 will not become dislodged and pinch off the fluid flow. Thus, the collection bag may be secured at both ends.

An exemplary expressor including an enclosed chamber is disclosed in International Publication No. WO 94/01193, which is incorporated by reference in its entirety.

In some embodiments, an expressor including an enclosed chamber may include an arrangement for moving fluid within the container, the arrangement including at least one of a) a drive mechanism for moving Container within the housing, or the housing, and b) an apparatus for pressing against a first portion of the container, as disclosed in, for example, International Publication No. WO 94/01193.

In some embodiments, for example, with respect to the systems illustrated in FIGS. 8 and 9, other pressure differential generators including, but not limited to, pumps such as peristaltic pumps and the like, may also be suitable. Alternatively, a container of biological fluid may be placed in a conventional expressor lacking an enclosed chamber (e.g., having an open chamber and at least one movable plate), and the expressor may be activated to direct fluid flow from the container toward the separation device 200.

SEPARATION DEVICE

As illustrated in the Figures, embodiments of the separation device 200 which comprises a separation medium 16 including a first surface 16a and a second surface 16b, provide for the processing of a biological fluid including plasma and at least one other component of the biological fluid to separate biological fluid into a plasma-rich fluid or fraction and a plasma-depleted fluid or fraction.

Figure 3:
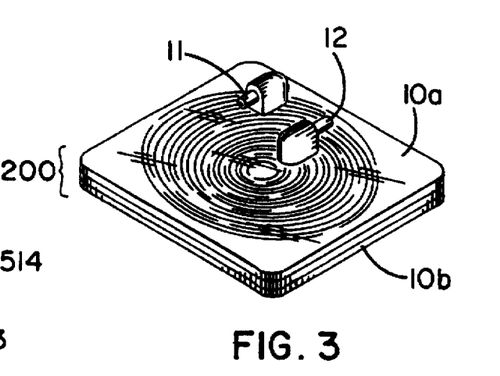
FIG. 3 is an oblique view of an embodiment of a separation device of the present invention.
Figure 4:
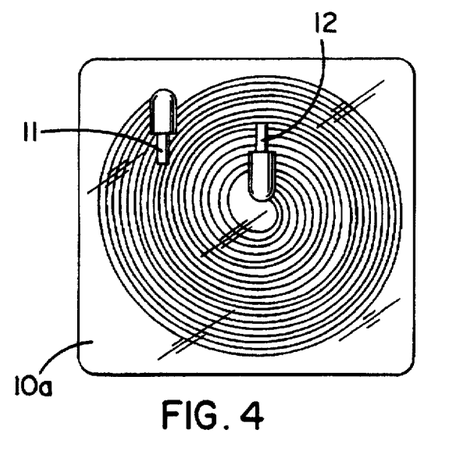
FIG. 4 is a top plan view of a first portion of the housing of the embodiment of FIG. 3.
Figure 10:
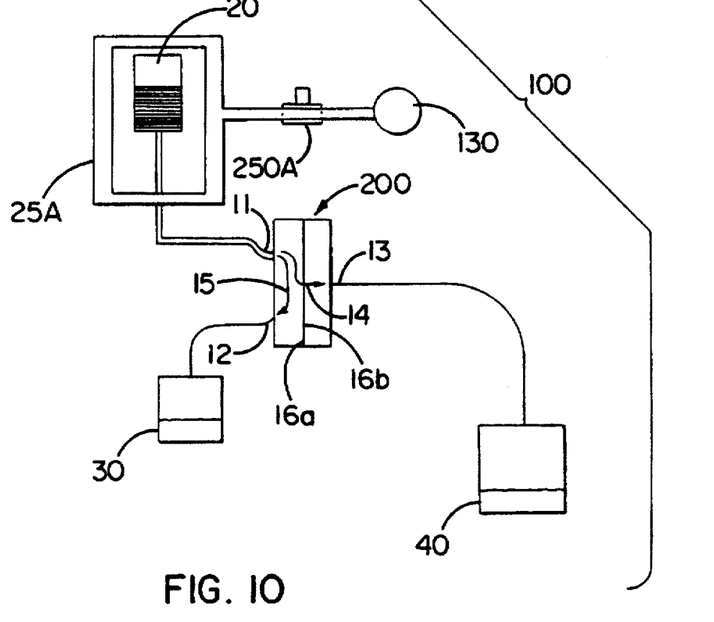
FIG. 10 is a schematic representation of another embodiment of a system according to the present invention.

In separation device 200 (e.g., as illustrated in FIG. 3), the housing 10 preferably includes first and second portions 10a and 10b, and the separation medium 16 is positioned inside the housing 10 between the first and second housing portions 10a, 10b, as shown in FIGS. 2 and 10. The first and second housing portions 10a, 10b may be joined in any convenient manner, for example, by ultrasonic or heat welding, an adhesive, a solvent, or one or more connectors.

The separation device 200 provides for directing a biological fluid along at least one spiral first flow path 15 along a first surface 16a of the separation medium, so that plasma-rich fluid passes along at least one second flow path 14 from the first surface of the separation medium 16a to the second surface of the separation medium 16b, and plasma-depleted fluid passes along the at least one spiral flow path 15 along the first surface of the medium. In a preferred embodiment, the separation device 200 includes fluid flow channels which separate the inlet flow of biological fluid into a plurality of separate spiral first flow paths along the first surface 16a of the separation medium 16.

Even more preferably, separation device 200 directs a plasma-depleted fluid tangentially or in a crossflow manner along first spiral flow path 15 across the first surface of the separation medium, while at the same time directing a portion of plasma-rich fluid along at least one second flow path 14 through the separation medium.

Figure 5:
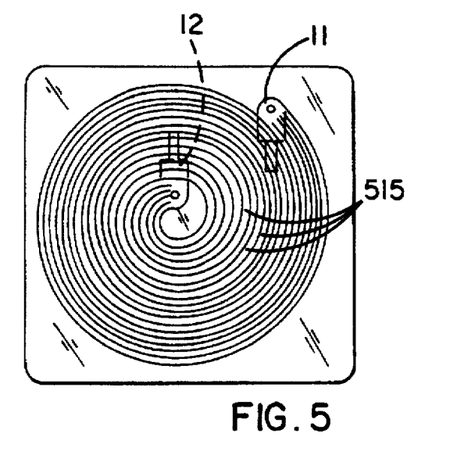
FIG. 5 is a bottom plan view of the first portion of the housing of FIG. 4, showing the first fluid flow path, including a plurality of fluid flow channels, in a separation device as provided by the invention.
Figure 6:
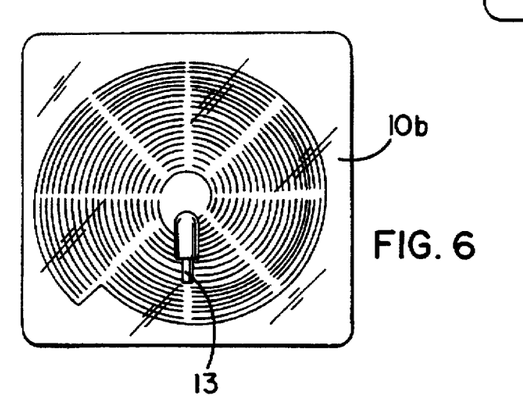
FIG. 6 is a bottom plan view of a second portion of the housing of the embodiment of FIG. 3.

In the embodiment illustrated in FIG. 5, first fluid flow path 15 includes at least one, and more preferably, two or more, spiral fluid flow channels 515, so that fluid may be spirally directed along surface 16a along or through the flow channel(s).

The term "spiral" may be defined in many ways, but one simple definition is that a spiral is the path of a point in a plane moving around a central point in the plane while continuously receding from or advancing toward the central point. In accordance with the invention, suitable types of spirals include, for example, involute, hyperbolic, logarithmic, and Archimedean.

The spiral fluid flow channels preferably maintain optimal pressure and fluid flow across the face of the separation medium. The use of at least one spiral fluid flow channel in accordance with the invention provides for utilizing a substantial portion of the separation medium, ensuring a sufficiently total area contact between the biological fluid and the separation medium, and maintaining a sufficient flow of biological fluid to minimize or prevent clogging and/or fouling of the separation medium. The use of spiral fluid flow channels also allow efficient processing while reducing the size of the separation device.

It is believed that spirally directing fluid flow maintains a uniformly high velocity of the fluid across the entire surface of the separation medium, and thus reduces or eliminates the development of eddies or stagnant areas of the biological fluid where platelets, red cells, or other material may settle upon, stick to, and foul the separation medium. Additionally, as noted earlier, the use of spiral flow channels also minimizes stress to the components of the biological fluid, and/or provides for a more compact separation device.

Preferably, a plurality (e.g., three or more) of spiral fluid flow channels are utilized so as to induce a uniformly high local fluid velocity along the entire immediate membrane surface and sweep clean the surface of the separation medium and prevent platelets, red cells, or other material from fouling the medium. Thus, platelet adhesion and/or red cell collection on or in the separation medium is minimized. Additionally, the use of several spiral fluid flow channels helps to fix the separation medium in place and to prevent sagging of the membrane due to the applied pressure.

Figure 7:
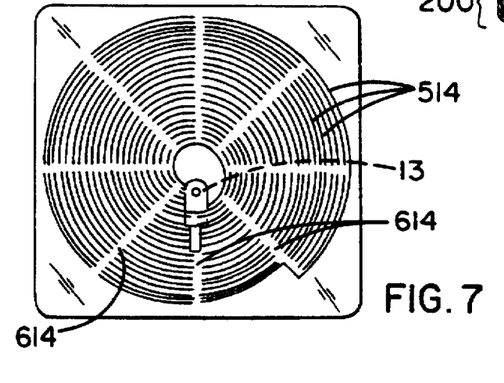
FIG. 7 is a top plan view of the second portion of the housing of FIG. 6, showing the second fluid flow path, including a plurality of fluid flow channels, in a separation device as provided by the invention.

Fluid flow channels may also be utilized on the side of the separation medium opposite the biological fluid tangential flow to control the flow rate and pressure drop of the plasma-rich fluid, such as plasma, as it passes along second fluid flow path 14. Preferably, second fluid flow path 14 includes two or more fluid flow channels 514, which may be parallel, curved, radial or serpentine in configuration. In a more preferred embodiment, as illustrated in FIG. 7, second fluid flow path 14 includes a plurality of spiral fluid flow channels 514.

The separation device may include an arrangement of ribs, walls or projections or may comprise one or more channels, grooves, conduits, passages, or the like which may be serpentine, parallel, curved, radial, spiral, or have a variety of other configurations facing the first surface 16a and/or facing the second surface 16b of the separation medium. The ribs, walls or projections may be used to define the channels, grooves, conduits, or passages and/or may support or position the separation medium 16 within the housing 10. In some embodiments, the separation device may include a chamber facing at least one surface of the separation medium. For example, the separation device may include a first shallow chamber facing the first surface 16a of the separation medium 16, and/or a second shallow chamber facing the second surface 16b of the medium 16.

In a preferred embodiment, at least two first fluid flow channels 515 face the first surface 16a of the separation medium. The first fluid flow channels 515 may be of any suitable design and construction. For example, the channels may have a rectangular, triangular, or semi-circular cross section and a constant or variable depth and/or width. The channels 515 may vary in depth and/or width, for example, between inlet 11 and outlet 12. In one embodiment, channels having a tapering depth, e.g., becoming more shallow toward the outlet, may provide for a more constant fluid velocity as the fluid passes through the channel and portions of the fluid pass through the separation medium.

Typically, at least one second fluid flow channel 514 faces the second surface 16b of the separation medium. However, in one embodiment, the separation device may include an arrangement of ribs, walls or projections that face the second surface 16b of the separation medium, without defining channels, grooves, conduits or passages. Preferably, two or more second fluid flow channels 514 face the second surface 16b of the medium. The second fluid flow channels 514 may be of any suitable design and construction. For example, the channels may have a rectangular, triangular, or semi-circular cross section and a constant or variable depth and/or width. The channels may vary in depth and/or width, for example, between the inlet portion of second flow channel 514, and the outlet portion of the channel, i.e., at outlet 13. For example, in some embodiments, second flow channels 514 having a tapering depth, e.g., becoming deeper toward the outlet, may provide for a more constant fluid velocity as more fluid passes through the separation medium and into the second fluid flow channels 514.

An exemplary average channel depth, which may be a constant depth, may be in the range from about 0.635 cm (about 0.250 inch) to about 0.0025 cm (about 0.001 inch). A more preferable average depth is in the range from about 0.02 cm (about 0.008 inch) to about 0.10 cm (about 0.04 inch), more preferably, about 0.02 cm (about 0.008 inch) to about 0.051 cm (about 0.02 inch).

In one embodiment, wherein first fluid flow channels 515 have a tapering depth, the depth varies from about 0.10 cm (about 0.040 inch) near the inlet portion of the flow channel, to about 0.02 cm (about 0.008 inch) near the outlet portion of the channel. More preferably, the depth varies from about 0.05 cm (about 0.02 inch) to about 0.02 cm (0.008 inch) from the inlet portion to the outlet portion of the first fluid flow channels 515. Even more preferably, the depth varies from about 0.04 cm to about 0.03 cm (about 0.015 inch to about 0.011 inch) from the inlet portion to the outlet portion.

An exemplary average channel width, which is preferably a constant width, may be in the range from about 0.635 cm (about 0.250 inch) to about 0.025 cm (about 0.010 inch).

The separation device may include additional channels, grooves, conduits, passages or the like. For example, as illustrated in FIG. 7, the separation device may include at least one radial channel 614 communicating with second fluid flow channel 514.

In some embodiments of the invention, there may be more ribs or walls facing the second or downstream surface 16b of the separation medium than facing the first or upstream surface 16a, to prevent deformation of the separation medium caused by the pressure differential between the upstream and downstream surfaces of the medium.

In other embodiments, areas of a surface of the separation medium, for example, areas of the upstream surface, may be secured to the housing. Among other advantages, such an arrangement may prevent deformation of the separation medium and/or the housing caused by the pressure differential through the medium. Alternatively or additionally, the housing may include projections, ribs or walls arranged facing the downstream surface of the medium to minimize deformation of the medium and/or housing resulting from the pressure differential. In one embodiment, the medium may be ultrasonically welded to those sections of the walls of the channels that face the upstream surface of the separation medium. Accordingly, these sections of the walls act as sacrificial ribs or energy directors.

The housing and the separation medium of the present inventive device may be of any suitable configuration and material. For example, the housing, including the channels, ribs, walls, and/or projections may be formed from a material that is substantially impermeable to the biological fluid and substantially unreactive with the biological fluid. Alternatively, the channels may be defined by two substantially impermeable and substantially unreactive sides and two permeable sides. For example, in one configuration, the opposing sides of a channel may each face a separation medium, allowing plasma-rich fluid to flow through each separation medium, and plasma-depleted fluid to flow tangentially to each separation medium. In another variation, e.g., involving a half-round configuration, at least one side of the channel is substantially impermeable to and substantially unreactive with the biological fluid.

In a preferred embodiment, the device has one inlet and two outlets. In an even more preferred embodiment, as illustrated in FIGS. 4–7, the biological fluid inlet 11 leading along the first surface of the separation medium is offset from the plasma-rich fluid outlet 13 facing the second surface of the separation medium. In some embodiments, such an arrangement may provide for better priming of the device.

However, other configurations can be employed without adversely affecting the proper functioning of the device. For example, multiple inlets for a biological fluid may be used so long as the biological fluid flows tangentially to the face of the separation medium. Alternatively, a single inlet and a single outlet may be used. For example, a separation device may be configured to provide for two liquid flow paths such that both liquid flow paths communicate with the inlet, but only one liquid flow path communicates with both the inlet and the outlet.

The separation medium 16 may be arranged in the separation device in any suitable manner so long as the biological fluid flow along the first surface 16a of the separation medium is maintained to a sufficient extent to minimize stress, damage, and/or loss of the components of the biological fluid. Preferably, the flow is maintained at a sufficient extent to avoid or minimize platelet adhesion to the separation medium and/or to avoid or minimize red blood cell damage (e.g., hemolysis).

One skilled in the art will recognize that platelet adhesion and/or red cell damage may be controlled or affected by manipulating any of a number of factors: velocity of the fluid flow, configuration of the channel, depth and/or width of the channel, varying the depth and/or varying the width of the channel, the surface characteristics of the separation medium, the smoothness of the medium's surface, and/or the angle at which the fluid flow crosses the face of the separation medium, among other factors. One skilled in the art will recognize that a desired velocity may be achieved by manipulating these and other elements.

Typically, a separation medium having a smooth surface may be preferable to a medium having a rougher surface, since platelets may not adhere as readily to a smoother surface. A smoother surface may also be suitable for processing a red cell-containing fluid, as it may minimize or prevent red cell damage and/or minimize the passage of red cells through the medium.

There are a variety of techniques for determining the smoothness of the surface of the separation medium. For example, a stylus may be drawn across the surface of the medium being measured, and variations are measured in the position of the stylus in directions normal to the surface. The smoothness of the surface is quantified by an average deviation of the stylus position from a mean position in microns. One machine for carrying out such a measurement is a Minutoyo Surftest 401 tally surf machine (Minutoyo Co. Ltd. UK). Other techniques and machines are also suitable. In some embodiments wherein a smoother surface is desirable, an exemplary smoothness is less than about 0.5 microns.

SEPARATION MEDIUM

A separation medium, as provided by the present invention, is suitable for processing a biological fluid so that the biological fluid may be separated into a plasma-depleted fraction or component and a plasma-rich fraction or component. For example, separation media in accordance with the invention separate a portion of plasma from a biological fluid containing platelets and/or red blood cells, typically whole blood or PRP, by allowing plasma to pass through the separation medium, while passing plasma and at least one of platelets and red blood cells along the first surface of the separation medium. The separation medium, as used herein, may include but is not limited to polymeric fibers (including hollow fibers), polymeric fiber matrices, polymeric membranes, and solid porous media.

A separation medium according to the invention may exhibit a pore structure or arrangement, such as, for example, an effective pore size, that is generally or intrinsically smaller than the average size of platelets and/or red blood cells. For the separation of about one unit of whole blood, a typical separation device as provided by the invention includes an effective pore size smaller than platelets on the average, typically less than about 4 micrometers, preferably less than about 2 micrometers, even more preferably, about 1 micrometer, or less.

The separation medium preferably has a low affinity for proteinaceous component. This may enhance the likelihood that the plasma-rich fluid, e.g., platelet-free plasma, will exhibit a normal concentration of proteinaceous clotting factors, growth factors, and other needed components. The separation medium and device also enhances the likelihood that complement activation will be avoided.

In accordance with the invention, a separation medium formed of fibers may be continuous, staple, or melt-blown. The fibers may be made from any material compatible with a biological fluid and may be treated in a variety of ways to make the medium more effective. Also, the fibers may be bonded, fused, or otherwise fixed to one another, or they may simply be mechanically entwined. A separation medium, as the term is used herein, may refer to one or more porous polymeric sheets, such as a woven or non-woven web of fibers. With or without a flexible porous substrate, or may refer to a membrane formed, for example, from a polymer solution in a solvent by precipitation of a polymer when the polymer solution is contacted by a solvent in which the polymer is not soluble. The separation medium may be manufactured from a variety of polymeric materials using different processes, including, but not limited to solvent casting, stretching, or etching. In one exemplary process, polycarbonate and/or polyester materials are irradiated, etched, and fabricated into finished products.

A preferred separation medium of this invention may be formed, for example, from any synthetic polymer capable of forming fibers or a membrane. Preferred polymers include, but are not limited to polyolefins, polyesters, and polyamides, e.g., polybutylene terephthalate (PBT) and nylon. A polymeric membrane may also be formed from a fluorinated polymer such as polyvinylidene difluoride (PVDF). The most preferred separation media include microporous polyamide membranes and polycarbonate membranes. For example, in some embodiments, e.g., involving a separation device for processing PRP, a suitable separation medium may include a nylon membrane. In other embodiments, e.g., involving a separation device for processing a red cell-containing fluid, a polycarbonate membrane may be desirable.

In those embodiments including treating and/or modifying the separation medium, an exemplary protocol includes surface modifying the medium, typically by radiation grafting or gas plasma treatment, in order to achieve the desired performance characteristics, whereby platelets and/or red cells are passed along the first surface of the medium with a minimum of medium blocking and/or with a minimum of damage to the platelets and/or red cells. It may also be desirable to surface modify the separation medium such that the resulting plasma solution contains essentially all of its native proteinaceous constituents.

Exemplary membranes having a low affinity for proteinaceous substances are disclosed in U.S. Pat. Nos. 4,886,836; 4,906,374; 4,964,989; 4,968,533; and 5,019,260. Other exemplary separation media include but are not limited to those disclosed in International Publication Nos. WO 92/07656 and WO 93/08904. Additionally, other media, including media commercially available from, but not limited to, Poretics Corporation (Livermore, Calif.), Nuclepore Corporation (Pleasanton, Calif.) or Costar Corporation, including nuclear particle track-etched membranes, may also be suitable. These commercially available media may be modified and/or treated as set forth above.

A typical separation device as provided by the invention includes a separation medium having an effective surface area in the range of about 1.94 $cm^2$ to about 290 $cm^2$ (about 0.3 $in^2$ to about 45 $in^2$). As used herein, the term effective surface area refers to the surface area contacted by the biological fluid.

In some embodiments, e.g., wherein the biological fluid is PRP, the effective surface area is in the range of about 13 $cm^2$ to about 52 $cm^2$ (about 2 $in^2$ to about 8 $in^2$). In other embodiments, e.g., wherein the biological fluid is a red cell-containing fluid such as whole blood or platelet-depleted blood, the effective surface area is in the range of about 65 $cm^2$ to about 271 $cm^2$ (about 10 $in^2$ to about 42 $in^2$).

A preferable ratio of the wetted surface area of the fluid flow channel to the volume of the channel (A/V) is in the range of about 6.3 $cm^{-1}$ to about 866 $cm^{-1}$ (about 16 $in^{-1}$ to about 2,200 $in^{-1}$), more preferably, about 6.3 $cm^{-1}$ to about 200 $cm^{-1}$ (about 16 $in^{-1}$ to about 508 $in^{-1}$), even more preferably, about 35 $cm^{-1}$ to about 69.5 $cm^{-1}$ (about 89 $in^{-1}$ to about 176.5 $in^{-1}$).

The permeability and size of a typical separation device as provided by the present invention is preferably sufficient to produce about 160 cc to about 240 cc of plasma at reasonable pressures (e.g., less than about $6.9 \times 10^5$ Pa (about 100 psi), preferably, less than about $1.4 \times 10^5$ Pa (about 20 psi), more preferably, less than about $6.9 \times 10^4$ Pa (about 10 psi), in a reasonable amount of time (e.g., less than about one hour). In some embodiments, particularly involving passing a red cell-containing fluid through the separation device, a preferred pressure is about $3.4 \times 10^4$ Pa or less (about 5 psi, or less).

The permeability of the separation medium is sufficient to allow the passage of a desirable amount of a fluid therethrough at a reasonable pressure in a reasonable amount of time. With respect to biological fluid, a preferred permeability is in the range of from about 0.00039 L/min/Pa/$m^2$ to about 0.023 L/min/Pa/$m^2$ (about 0.25 to about 15.0 L/min/psid/$ft^2$). With respect to plasma, a preferred permeability is in the range of from about 0.00039 L/min/Pa/$m^2$ to about 0.0078 L/min/Pa/$m^2$ (about 0.25 to about 5.0 L/min/psid/$ft^2$), more preferably in the range of about 0.0011 L/min/Pa/$m^2$ to about 0.0047 L/min/Pa/$m^2$ (about 0.7 to about 3.0 L/min/psid/$ft^2$).

As provided by the present invention, all of these typical parameters may be varied to achieve a desired result, e.g., varied preferably to minimize platelet and/or red cell loss, to maximize plasma-rich fluid production, and/or to establish a certain flow rate.

In some embodiments, particularly in those including the use of at least two expressors including enclosed chambers, other separation devices and assemblies, including, for example, those disclosed in International Publication Nos. WO 93/08904 and WO 92/07656, may be used to produce a plasma-rich fluid and/or a plasma-depleted fluid in accordance with the invention. With respect to FIG. 1, a separation device without at least one spiral flow channel may be interposed between containers 20 and 30. Illustratively, in some embodiments, a suitable separation device may provide for a first flow path along a first surface of at least one separation medium including at least one, and preferably two or more, parallel, radial or serpentine flow channels, rather than at least one spiral flow channel. In these embodiments, the separation device may include a separation medium comprising one or more planar membranes or hollow fibers.

In some embodiments, at least one separation device includes a separation medium that is capable of rotation during use. Illustratively, at least one of the separation devices including rotatable separation media such as the membrane filter apparatus disclosed in International Publication No. WO 93/24157 and U.S. Pat. No. 5,034,135 may be suitable.

A system as provided by the present invention may be used in conjunction with other devices, assemblies, and/or systems, including but not limited to, automated systems, filtration and/or separation devices, vents and gas manipulation devices, such as gas inlets, gas outlets, and gas collection and displacement loops. Preferred filtration devices or assemblies include leukocyte depletion devices and/or red cell barrier devices, as disclosed in, for example, U.S. Pat. Nos. 4,880,548; 4,925,572; 4,985,153; 5,100,564; 5,152,905; 5,217,627; 5,229,012, or commercially available devices available from, for example, Pall Corporation (East Hills, N.Y.). Exemplary leukocyte depletion devices from Pall Corporation include those available as PL 100™ and BPF4™.

Preferred vents and gas manipulation devices include those disclosed in, for example, U.S. Pat. Nos. 5,217,627, 5,126,054; and International Publication Nos. WO 92/07656, WO 91/17809 and WO 93/25295. An exemplary automated system is disclosed in International Publication No. WO 94/01193.

The present inventive device may be part of an apheresis system, including a battery operated and/or automated apheresis system. The sizes, nature, and configuration of the present inventive device can be adjusted to vary the capacity of the device to suit its intended environment.

METHOD

The processing of biological fluid in the context of the present invention may take place at any suitable time, which may be soon after donation. For example, when the biological fluid is donated whole blood, it is typically processed as soon as practicable in order to maximize the number of components derived and to maximize blood component viability and physiological activity. Early processing may more effectively reduce or eliminate contaminating factors, including, but not limited to, leukocytes and microaggregates.

Typically, a biological fluid, e.g., a unit of donated whole blood or platelet-rich plasma (PRP), is collected in a container such as a conventional blood collection bag or a satellite bag. As will be noted in more detail below, biological fluid or a portion thereof may be passed from the collection bag to a separation device to produce a plasma-rich fraction and/or a plasma-depleted fraction, or the biological fluid may be passed to at least one satellite bag before passing the fluid to the separation device.

The biological fluid may be depleted of leukocytes, e.g., passed through a device such as a leukocyte depletion filter assembly or a leukocyte and platelet depletion filter assembly, before or after collecting the fluid in the container. For example, the biological fluid, e.g., whole blood or PRP, may be collected in a container, passed through a fibrous leukocyte depletion filter assembly, and the leukocyte depleted fluid may be collected in another container such as a satellite bag, before passing the fluid through separation device.

Exemplary methods as provided by the invention may be described in more detail by referring to the Figures, particularly FIGS. 1, 2, and 8–10. Movement of the biological fluid through the device and/or through the system may be effected by maintaining a pressure differential between a container 20 such as a collection bag, and the destination of the biological fluid (e.g., a container 30 such as a satellite bag), to cause the fluid to flow in a desired direction. Exemplary protocols for creating this pressure differential include utilizing a gravity head, applying pressure to the container (e.g., by hand or with an expressor plate or a pressure cuff), and by placing the collection and/or the satellite bag in a chamber, preferably an enclosed chamber, and establishing a pressure differential between the satellite bag and the collection bag, e.g., through the use of a vacuum chamber or a pump. As will be noted in more detail below, in some embodiments, a plurality of pressure differentials, e.g., first and second, or alternating pressure differentials, may be created to repeatedly direct the flow of fluid through the separation device 200. In one embodiment of the invention, each of the first or collection container 20 and the additional or satellite container 30 may be associated with a separate pressure differential generator. For example, in a preferred embodiment as illustrated in FIG. 1, each of the first or collection container 20 and the additional or satellite container 30 is associated with a pressure differential generator 25A and 25B wherein each pressure differential generator comprises an expressor including an enclosed chamber for containing a variable volume container suitable for holding a biological fluid. In another embodiment, containers 90, 20 and 30 may each be associated with an expressor including an enclosed chamber for containing the container.

In a preferred method in accordance with the invention, the pressure differential generators 25A and 25B comprise expressors including enclosed chambers, and the expressors may be activated and deactivated, so that biological fluid may be repeatedly directed through the separation device 200. Preferably, activating and deactivating the expressors may include using flow control devices 250A and 250B such as three-way valves, so that one expressor may be placed in fluid communication with a pressure regulating mechanism 130 to activate the expressor, and the other expressor may be placed in fluid communication with the ambient atmosphere to deactivate this second expressor.

For example, a first container 20 including a biological fluid (e.g., whole blood or PRP) may be placed within the enclosed chamber of pressure differential generator 25A, and an empty second container 30 may be placed within the enclosed chamber of pressure differential generator 25B. Pressure differential generator 25A may be activated by placing it in fluid communication with pressure regulating mechanism 130 through flow control device 250A and conduits 60A and 60B, and flow control device 250B may be arranged so that expressor 25B is in fluid communication with the ambient atmosphere.

Once expressor 25A is activated, and the pressure within the enclosed chamber is varied, the volume of container 20 is varied (e.g., the container is compressed), causing biological fluid to flow from the container 20, through conduit 61, flow control device 300, to separation device 200 through inlet 11. Biological fluid is passed along the first fluid flow path 15, i.e., along the first surface of the separation medium, so that plasma-depleted fluid passes along the first surface of the separation medium on the way to first outlet 12; and a portion of plasma-rich fluid passes along the second fluid flow path 14, i.e., through the separation medium, on the way to outlet 13.

Preferably, the biological fluid is directed to flow tangentially or parallel along the first surface 16a of the separation medium. Directing the biological fluid along the separation medium may include channelling the biological fluid tangentially along the surface of the separation medium. This permits the passage of plasma-depleted fluid along the first surface of the medium, and the passage of plasma-rich fluid through the medium, while reducing the tendency for cellular components and/or platelets to adhere to the surface of the medium. Accordingly, clogging or fouling of the separation medium is prevented or reduced.

As the biological fluid continues along the first flow path 15 along the first surface 16a of the separation medium 16, more and more plasma-rich fluid crosses the separation medium 16. A plasma-depleted fluid, e.g., a platelet-containing and/or red cell-containing fluid, then exits the housing 10 at the first outlet 12 while plasma-rich fluid exits the housing 10 at the second outlet 13.

In the embodiment illustrated in FIG. 1, plasma-rich fluid passes through outlet 13, through conduit 69, and into satellite container 40. Plasma-depleted fluid passes through outlet 12, through conduit 64, through flow control device 300 and conduit 66, and into container 30, located within the chamber of expressor 25B.

Once container 20 has emptied, and container 30 has filled with plasma-depleted fluid, expressor 25A may be deactivated, e.g., placed in fluid communication with the ambient atmosphere through flow control device 250A, and pressure differential generator 25B, comprising an expressor including an enclosed chamber, may be activated by placing it in fluid communication with pressure regulating mechanism 130 through flow control device 250B and conduits 60C and 60D. Once expressor 25B is activated and the pressure within the enclosed chamber is varied, the volume of container 30 is varied (e.g., the container is compressed), causing plasma-depleted fluid to be re-directed from container 30, through conduits 66 and 68, flow control device 300, conduit 67, and into inlet 11. The fluid passes along the first surface 16a of the separation medium 16 in the separation device 200, so that plasma-depleted fluid passes from outlet 12, through conduits 64 and 63, flow control device 300, conduits 62 and 61, and into container 20. Additional plasma-rich fluid passes from outlet 13, through conduit 69, and into container 40.

In a preferred embodiment, regardless of which pressure differential generator is activated or deactivated, the fluid is always passed through inlet 11 to outlet 12. For example, as illustrated in FIG. 1, flow control devices 300 such as one-way check valves may be arranged so that fluid may be passed from either of containers 20 or 30 to the inlet 11 and then the outlet 12, without fluid passing from outlet 12 toward inlet 11. Additionally, the positive pressure in the conduits allows the fluid to flow in the desired direction through the system.

in another embodiment, the plasma-depleted fluid may be passed from container 30 in the opposite direction with respect to the first surface of the separation medium, i.e., through outlet 12 to inlet 11.

In accordance with other embodiments of the invention, for example, as illustrated by FIGS. 8 and 9, a pressure differential generator 500 such as a peristaltic pump or an expressor lacking an enclosed chamber may be utilized to direct the biological fluid from the first container 20 through inlet 11 to the first surface 16a of the separation medium 16 in the separation device 200. In another embodiment, as shown in FIG. 10, a pressure differential generator 25A such as an expressor including an enclosed chamber as described with respect to FIG. 1 may be used to direct the biological fluid from the first container 20 through the separation device 200 to a second container 30 not in an expressor.

With respect to the preferred embodiment of a separation device, which is illustrated in FIGS. 3–7, and may be used in the exemplary illustrated systems, biological fluid may be passed from first container 20, through inlet 11 of separation device 200, and spirally directed along two or more flow paths, e.g., along spiral channels 515 along the first surface 16a of the separation medium. Preferably, biological fluid is spirally channelled along a plurality of flow paths 515 so that plasma-depletable fluid passes tangentially across the first surface 16a of the separation medium 16, and plasma-rich fluid passes through the separation medium, i.e., from the first surface 16a to the second surface 16b.

Typically, the plasma-rich fluid exiting at the second outlet 13, and/or the plasma-depleted fluid exiting at the first outlet 12, may be collected or recovered in separate containers. For example, as illustrated in FIGS. 1, 9, and 10, plasma-depleted fluid may be collected or recovered in first satellite bag 30, and plasma-rich fluid may be collected or recovered in second satellite bag 40.

In some embodiments, for example, as shown in FIGS. 1 and 8, plasma-depleted fluid collected in first satellite container 30 may be re-directed to the separation device to deplete additional amounts of plasma. The plasma-depleted fluid may be repeatedly recirculated through the separation device, e.g., until the plasma-depleted fluid in the collection or satellite bag 20, 30 (FIGS. 1 and 8) contains a predetermined amount or concentration of the desired component, e.g., platelets and/or red blood cells, or, until a desired amount of plasma-rich fluid is collected in the second satellite bag 40.

In other exemplary embodiments, e.g., involving platelet-depleted or platelet- and leukocyte-depleted biological fluid, recirculation may be repeated until the plasma depleted fluid contains a pre-determined amount or concentration of red blood cells.

In an embodiment, processing biological fluid in accordance with the invention includes depleting the biological fluid of leukocytes, for example, by passing the fluid, e.g., red cell-containing fluid such as whole blood, or platelet-containing fluid such as PRP, through a leukocyte depletion filter assembly including a leukocyte depletion medium.

For example, whole blood may be passed through a leukocyte depletion filter assembly as disclosed in, for example, U.S. Pat. Nos. 4,925,572, 5,229,012, or 4,985,153, or by using a commercially available filter, such as the filter available from Pall Corporation (East Hills, N.Y.) as BPF4™. Illustratively, with respect to FIG. 2, whole blood may be collected in a container 90, and passed through a leukocyte depletion filter assembly 95 to remove leukocytes, or leukocytes and platelets, and the filtered blood may be collected in a container 20. In one embodiment, the filter assembly 95 is separated while maintaining the sterility of the fluid in the container 20 and the system. Subsequently, as illustrated in FIG. 1, the fluid may be passed from container 20 to a separation device 200 as described previously, so that plasma is separated from the red blood cells and platelets, or plasma is separated from the red blood cells.

In an embodiment, container 90 may be a variable volume container suitable for placement within the enclosed chamber of a pressure differential generator. For example, a system according to the invention may include containers 90 and 20, leukocyte depletion filter assembly 95 interposed between the containers, conduits providing fluid communication between the containers and filter assembly, and enclosed pressure differential generators capable of enclosing containers 90 and 20. A flow control device such as a check valve interposed between the filter assembly 95 and the container 20. In this embodiment, once the enclosed pressure differential enclosing container 20 (which includes leukocyte depleted fluid) is activated, the check valve prevents the flow of fluid from container 20 to container 90. Accordingly, fluid may be passed from container 20 through separation device 200 and into container 30 (e.g., within enclosed pressure differential 25B).

Additionally, or alternatively, at least one leukocyte depletion filter assembly may be arranged upstream and/or downstream of the separation device 200, e.g., near inlet 11 and/or outlet 12; as well as downstream from plasma-rich outlet 13. Preferably, the leukocyte depletion filter assemblies are arranged in the system so that the fluid flows unidirectionally through an assembly. Of course, the separated components recovered or collected in containers 20, 30 and/or 40 may be passed through a leukocyte depletion filter assembly at any desirable time. Suitable leukocyte depletion filter assemblies include those discussed previously.

In those embodiments wherein the leukocyte depletion device also depletes or removes platelets from the fluid passing therethrough, the method may additionally include removing the retained platelets, with or without removal of the leukocytes. Illustratively, a different ionic environment may be created with respect to the leukocyte depletion medium, e.g., by contacting the leukocyte depletion medium with saline, to wash the platelets and leukocytes out of the medium. The platelet containing fluid may then be passed through a leukocyte depletion device as disclosed in, for example, U.S. Pat. Nos. 4,880,548, 5,100,564, and 5,152,905.

In some embodiments, a biological fluid such as whole blood may be collected in a container, and the blood may be separated into a supernatant layer and a sediment layer, typically by subjecting the fluid to centrifugation. The supernatant layer is then passed into a satellite container, preferably making sure to prevent any of the sediment layer from passing into the satellite container, either by clamping the conduit at the appropriate time, or by including in the system a red cell barrier medium or a red cell barrier/leukocyte depletion medium, such as the media disclosed in U.S. Pat. No. 5,152,905, and International Publication No. WO 93/25295. The supernatant layer is further processed by passing it through the separation device 200.

The biological fluid to be processed may be supplied in any suitable quantity consistent with the capacity of the overall device and by any suitable apparatus or device, e.g., in a batch operation by, for example, a blood bag connected to an expressor or a syringe, or in a continuous operation as part of, for example, an apheresis system. The biological fluid may be processed in an automated system as disclosed in, for example, International Publication WO 94/01193.

In accordance with the present invention, a pressure differential may be created in connection with a variety of systems that include separation devices, including apheresis systems. For example, two or more expressors including enclosed chambers may be utilized in connection with an apheresis system comprising at least one rotating membrane filter apparatus, including the automated apheresis systems and rotating membrane filter apparatus disclosed in International Publication No. WO 93/24157 and U.S. Pat. No. 5,034,135.

In order that the invention herein described may be more fully understood, the following examples are set out regarding use of the present invention. These examples are for illustrative purposes only and are not to be construed as limiting the present invention in any manner.

EXAMPLE 1

A unit of whole blood (approximately 500 ml) is passed through a BPF-4™ leukocyte depletion filter (Pall Corp., East Hills, N.Y.) into a plastic satellite bag, as illustrated in FIG. 2, to yield a unit of approximately 450 ml of leukocyte- and platelet depleted blood. The platelet removal efficiency is about 99%, and the leukocyte removal efficiency is >99.9%. A 100 ml aliquot of this filtered blood is separated into a plastic satellite bag, and this aliquot is then processed using a system as illustrated in FIG. 1. The hematocrit of this aliquot is about 36%.

The system includes two expressors, each including an enclosed chamber capable of enclosing a plastic satellite bag. Each expressor is connected, via a conduit, to a pressure source that provides a pressure of 5 p.s.i.g. A separate three-way valve is interposed between the pressure source and each expressor. Depending on the position of the three-way valve, the chamber can be pressurized or vented to the ambient atmosphere, as desired.

The system also includes two empty plastic satellite bags, a separation device (as described below), and conduits to provide fluid communication between the bags and the separation device. The system includes four one-way check valves in the conduits as illustrated in FIG. 1.

The bag of leukocyte- and platelet-depleted blood (hereinafter, the first bag) is placed in an enclosed chamber of one expressor, and an empty plastic satellite bag (hereinafter, the second bag) is placed in the enclosed chamber of the other expressor. The additional empty plastic bag, for collecting plasma (hereinafter, the third bag), is placed on a scale for weighing the bag and its contents.

The tubing exiting the first bag (clamped closed at this point) is connected to the inlet port of a separation device as shown in FIGS. 3–7. The tubing exiting the third bag is connected to the plasma outlet port of the device, and the tubing exiting the second bag is connected to the non-plasma outlet port of the device.

The separation medium is a microporous PVP-free polycarbonate membrane available from Poretics Corp. (Catalog No. 19430) having a pore rating of 0.4 microns. The membrane is gas plasma treated to provide a CWST of about 70 dynes/cm. The separation medium includes a downstream support layer, having polyester fibers with an average fiber diameter of about 10–25 microns, and a basis weight of approximately 15 g/M$^2$. The support layer is available from Mitsubishi International Corp. Textile Division, NY, N.Y., as Hirose 05TH15.

The housing for the separation device used in this Example includes spiral flow paths, as illustrated in FIGS. 3–7. The inlet half side of the housing includes 5 spiral flow channels in the shape of Archimedes spirals, each having a depth of 0.011 inch throughout the channel. The plasma outlet half side of the housing includes 5 spiral flow channels, each having a depth of 0.011 inch throughout the channel. The plasma outlet half side of the housing also includes eight radial channels communicating with the spiral flow channels.

The third bag is placed on a scale so that the amount of plasma entering the bag can be monitored.

The three-way valve leading to the first chamber (containing the first bag) is set so that the first chamber is pressurized, and the three-way valve leading to the second chamber (containing the empty second bag) is set so that the chamber is open to the ambient atmosphere. The clamp on the line leading from the first bag is opened, and blood is passed from the first bag, and into the separation device. Clear fluid exits the plasma port, and enters the third bag. Turbid (red cell containing) fluid exits the non-plasma port, and enters the second bag. Once the first bag is nearly empty, the three-way valves are re-set so that the second chamber is pressurized, and the first chamber is open to the atmosphere. Fluid passes from the second bag to the separation device. In view of the positive pressure in the conduits, and the arrangement of the check valves, the fluid enters the device through the inlet port. Once again, plasma exits the plasma port, and enters the third bag. Additionally, due to the positive pressure in the conduits and the arrangement of the check valves, fluid exits the non-plasma port and enters the first bag. Fluid is passed back and forth between the first and second bags by alternately activating and deactivating the expressors as described previously.

The flow rates are recorded after 3 minutes and every few minutes thereafter. At three minutes the initial flow rate is about 1.9 ml/min. The amount of plasma entering the third bag is recorded after each minute.

After approximately 45 minutes, and 16 total passes through the separation device, about 45 ml of plasma is collected in the satellite bag and about 45 ml of red cells are collected in the source bag. The final flow rate, i.e., at the last full minute prior to the end of the test, is about 0.5 ml/min. The hematocrit of the red cell solution is about 80%, and a hemolysis reading is negative.

The above result indicates that concentrated red cells and cell-free plasma can be recovered in a reasonable time, using recirculation of fluid, and without the use of peristaltic pumping, by a system provided by the invention.

While the invention has been described in some detail by way of illustration and example, it should be understood that the invention is susceptible to various modifications and alternative forms, and is not restricted to the specific embodiments set forth. It should also be understood that these specific embodiments are not intended to limit the invention but, on the contrary, the intention is to cover all modifications, equivalents, and alternatives falling within the spirit and scope of the invention.

We claim:

1. A method for treating a biological fluid comprising:

placing a first variable volume container of biological fluid including plasma and at least one other component of the biological fluid in an enclosed chamber of a first pressure differential generator, with at least a first conduit extending from the first container to the exterior of the chamber and providing fluid communication with a separation device;

said separation device comprising a housing including a biological fluid inlet, a plasma-depleted fluid outlet, a plasma-rich fluid outlet and a separation medium arranged within the housing, said medium arranged within the housing, said medium having a first surface and a second surface;

varying the pressure within the chamber which is exerted on the first container to vary the volume of the first container and force fluid out of the first container to the separation device via the first conduit;

spirally passing the biological fluid along at least one first flow path in the separation device along the first surface of the separation medium; and, passing a plasma-rich fluid along at least one second flow path through the separation medium and to the plasma-rich fluid outlet, and passing a plasma-depleted fluid along the first surface of the separation medium to the plasma-depleted fluid outlet;

passing the plasma-depleted fluid from the plasma-depleted fluid outlet to a second container suitable for containing the plasma-depleted fluid, the second container comprising a variable volume container, said second container being located in an enclosed chamber of a second pressure differential generator, with at least a second conduit extending from the second container to the exterior of the chamber and providing fluid communication with the separation device; and varying the pressure within the chamber which is exerted on the second container to vary the volume of the second container and force fluid out of the second container to the separation device via the second conduit.

2. The method of claim 1 comprising spirally passing plasma and red cells along the first surface of the separation medium.

3. The method of claim 1 further comprising passing at least one of the biological fluid, the plasma-rich fluid, and the plasma-depleted fluid, through a leukocyte depletion device.

4. The method of claim 1 further comprising recirculating the plasma-depleted fluid passed along the first surface of the separation medium back to the first surface of the separation medium.

5. The method of claim 1 comprising spirally passing plasma and platelets along the first surface of the separation medium.

6. The method of claim 1 further comprising passing plasma-depleted fluid along the first surface of the separation medium into the first container via the first conduit, and passing plasma-rich fluid from the first surface of the separation medium through the separation medium to the second surface of the separation medium.

7. The method of claim 1 wherein spirally passing the biological fluid along at least one flow path in the separation device comprises passing the biological fluid through at least one spiral flow channel having a greater depth proximal to the biological fluid inlet than proximal to the plasma-depleted fluid outlet.

8. A method for processing a biological fluid comprising:

placing a first variable volume container of a biological fluid including plasma and at least one other component of the biological fluid in an enclosed chamber of a first pressure differential generator, wherein at least a first conduit extends from the first container to the exterior of the chamber and provides fluid communication with a separation device comprising a housing and a separation medium having a first surface and a second surface;

placing a second variable volume container, suitable for holding a biological fluid including plasma and at least one other component of the biological fluid in an enclosed chamber of a second pressure differential generator, wherein at least a second conduit extends from the second container to the exterior of the chamber and provides fluid communication with the separation device;

varying the pressure within the chamber of the first pressure differential generator which is exerted on the first container to vary the volume of the first container and force fluid out of the first container to the separation device via the first conduit;

passing the biological fluid along at least one first fluid flow path in the separation device along the first surface of the separation medium; and, passing a plasma-rich fluid along at least one second fluid flow path from the first surface of the separation medium through the separation medium to a second surface of the separation medium, and passing a plasma-depleted fluid along the first fluid flow path along the first surface of the separation medium through the separation device, the second conduit, and into the second container in the enclosed chamber of the second pressure differential generator;

varying the pressure within the chamber of the second pressure differential generator which is exerted on the second container to vary the volume of the second container and force fluid out of the second container to the separation device via the second conduit.

9. The method of claim 8 wherein passing the fluid along the first fluid flow path comprises spirally passing fluid along two or more fluid flow channels.

10. A system for processing a biological fluid comprising:

a first pressure differential generator comprising a first enclosed chamber;

a first variable volume container suitable for holding a biological fluid arranged inside the first enclosed chamber;

at least a first conduit extending from the first container to the exterior of the first chamber; and, a separation device, in communication with the first conduit;

said separation device comprising a housing including a biological fluid inlet, a plasma-depleted fluid outlet, and a plasma-rich fluid outlet, and a separation medium arranged within the housing, said medium having a first surface and a second surface, said device providing at least one first fluid flow path leading from the biological fluid inlet to the first surface of the separation medium and to the plasma-depleted fluid outlet, and at least one second fluid flow path leading from the inlet through the separation medium to the plasma-rich fluid outlet, said first conduit in communication with the first fluid flow path;

a second pressure differential generator comprising a second enclosed chamber;

a second variable volume container suitable for holding a biological fluid arranged inside the second enclosed chamber;

at least a second conduit extending from the second container to the exterior of the second chamber, said second conduit in communication with the first fluid flow path of the separation device.

11. The device of claim 10 wherein the separation device includes at least one spiral first fluid flow path.

12. The system of claim 10 wherein the at least one spiral first flow path comprises at least one spiral flow channel having a greater depth proximal to the biological fluid inlet than proximal to the plasma-depleted fluid outlet.

13. A method for processing a biological fluid comprising:

activating a first expressor including an enclosed chamber and creating a first pressure differential and passing a biological fluid including plasma and at least one other component of the biological fluid from a first flexible container in the enclosed chamber to a separation device comprising a housing and a separation medium having a first surface and a second surface;

passing the biological fluid along at least one first fluid flow path in the separation device along the first surface of the separation medium; and, passing a plasma-rich fluid along at least one second fluid flow path from the first surface of the separation medium through the separation medium to a second surface of the separation medium, and passing a plasma-depleted fluid along the first fluid flow path along the first surface of the separation medium through the separation device, and into a second flexible container said second flexible container being disposed in an enclosed chamber of a second expressor;

activating the second expressor and creating a second pressure differential and passing the plasma depleted fluid from the second container in the enclosed chamber to the separation device.

14. The method of claim 13 wherein activating the second expressor and creating the second pressure differential includes passing the plasma-depleted fluid along the first fluid flow path in the separation device along the first surface of the separation medium;

passing plasma-rich fluid along the second fluid flow path from the first surface of the separation medium through the separation medium to the second surface of the separation medium, and passing plasma-depleted fluid along the first fluid flow path along the first surface of the separation medium through the separation device, and into the first container;

the method further including activating the first expressor and creating another first pressure differential and passing plasma-depleted fluid along at least one first fluid flow path in the separation device along the first surface of the separation medium; and, passing plasma-rich fluid along at least one second fluid flow path from the first surface of the separation medium through the separation medium to the second surface of the separation medium, and passing plasma-depleted fluid along the first fluid flow path along the first surface of the separation medium through the separation device, and into the second container.

* * * * *